United States Patent
Khachin et al.

(10) Patent No.: US 7,553,314 B2
(45) Date of Patent: *Jun. 30, 2009

(54) SURGICAL DEVICE FOR RETRIEVAL OF FOREIGN OBJECTS FROM A BODY

(75) Inventors: Stepan Khachin, Tomsk (RU); Vladimir Khachin, Tomsk (RU)

(73) Assignee: Lithotech Medical, Ltd., Katzrin (IL)

( * ) Notice: Subject to any disclaimer, the term of this patent is extended or adjusted under 35 U.S.C. 154(b) by 340 days.

This patent is subject to a terminal disclaimer.

(21) Appl. No.: 11/493,745

(22) Filed: Jul. 27, 2006

(65) Prior Publication Data

US 2006/0264974 A1 Nov. 23, 2006

Related U.S. Application Data

(63) Continuation of application No. 10/216,672, filed on Aug. 12, 2002, now Pat. No. 7,101,380.

(30) Foreign Application Priority Data

Jun. 28, 2001 (WO) .................. PCT/IL01/00591

(51) Int. Cl.
*A61B 17/22* (2006.01)
(52) U.S. Cl. ...................... 606/127; 606/200
(58) Field of Classification Search .............. 606/106, 606/127, 128, 200
See application file for complete search history.

(56) References Cited

U.S. PATENT DOCUMENTS

| | | | |
|---|---|---|---|
| 3,472,230 A | 10/1969 | Fogarty | |
| 3,496,330 A | 2/1970 | Needham | |
| 4,347,846 A | 9/1982 | Dormia | |
| 4,425,908 A | 1/1984 | Simon | |
| 4,619,246 A | 10/1986 | Molgaard-Neilsen et al. | |

(Continued)

FOREIGN PATENT DOCUMENTS

FR 1197808 12/1959

(Continued)

OTHER PUBLICATIONS

XP-002172655: Abstract for RU2022528, Sveshnikov, A. et al, "Instrument remove Stone Ureter Cage Made Branch Support Cable Enclose Withdraw Stone," Nov. 15, 1994.

*Primary Examiner*—Todd E Manahan
*Assistant Examiner*—Michael G Mendoza
(74) *Attorney, Agent, or Firm*—Browdy and Neimark, P.L.L.C.

(57) ABSTRACT

A surgical device for removing a foreign object from a body is described. The device includes a retrieval basket for entrapping and retaining the object located in the body, a basket control assembly comprising a tubular sheath adapted to penetrate into the body for reaching the object, and a manipulator for manipulating the basket for extraction the object from the body. The basket comprises a structure having a proximal end and a distal end. The structure is formed by a plurality of filaments fabricated from a single or several wires. The filaments extend from the proximal end towards the distal end. At least a part of the filaments are configured in the form of loops. At least a part of the loops are interlaced so as to define a net at the distal end, and thereby impart structural rigidity and dilatation ability to the basket when opened.

38 Claims, 14 Drawing Sheets

U.S. PATENT DOCUMENTS

| | | | |
|---|---|---|---|
| 4,790,812 A | 12/1988 | Hawkins, Jr. et al. |
| 5,064,428 A | 11/1991 | Cope et al. |
| 5,496,330 A | 3/1996 | Bates et al. |
| 5,658,296 A | 8/1997 | Bates et al. |
| 5,792,145 A | 8/1998 | Bates et al. |
| 5,895,398 A | 4/1999 | Wensel et al. |
| 5,928,260 A | 7/1999 | Chin et al. |
| 6,093,196 A | 7/2000 | Okada |
| 6,159,220 A | 12/2000 | Gobron et al. |
| 6,168,603 B1 | 1/2001 | Leslie et al. |
| 6,183,482 B1 | 2/2001 | Bates et al. |
| 6,190,394 B1 | 2/2001 | Lind et al. |
| 6,224,612 B1 | 5/2001 | Bates et al. |
| 6,302,895 B1 | 10/2001 | Gobron et al. |
| 6,344,048 B1 | 2/2002 | Chin et al. |
| 6,348,056 B1 | 2/2002 | Bates et al. |
| 6,350,266 B1 | 2/2002 | White et al. |
| 6,368,328 B1 | 4/2002 | Chu et al. |
| 6,511,492 B1 | 1/2003 | Rosenbluth et al. |
| 6,514,273 B1 | 2/2003 | Voss et al. |
| 6,527,781 B2 | 3/2003 | Bates et al. |
| 6,610,077 B1 | 8/2003 | Hancock et al. |
| 6,626,915 B2 | 9/2003 | Leveillee |
| 6,752,811 B2 | 6/2004 | Chu et al. |

FOREIGN PATENT DOCUMENTS

| | | |
|---|---|---|
| SU | 1036325 | 5/1981 |
| SU | 2022528 | 2/1992 |
| WO | WO 92/16153 | 10/1992 |
| WO | WO 96/23446 | 8/1996 |
| WO | WO 01/10290 | 2/2001 |

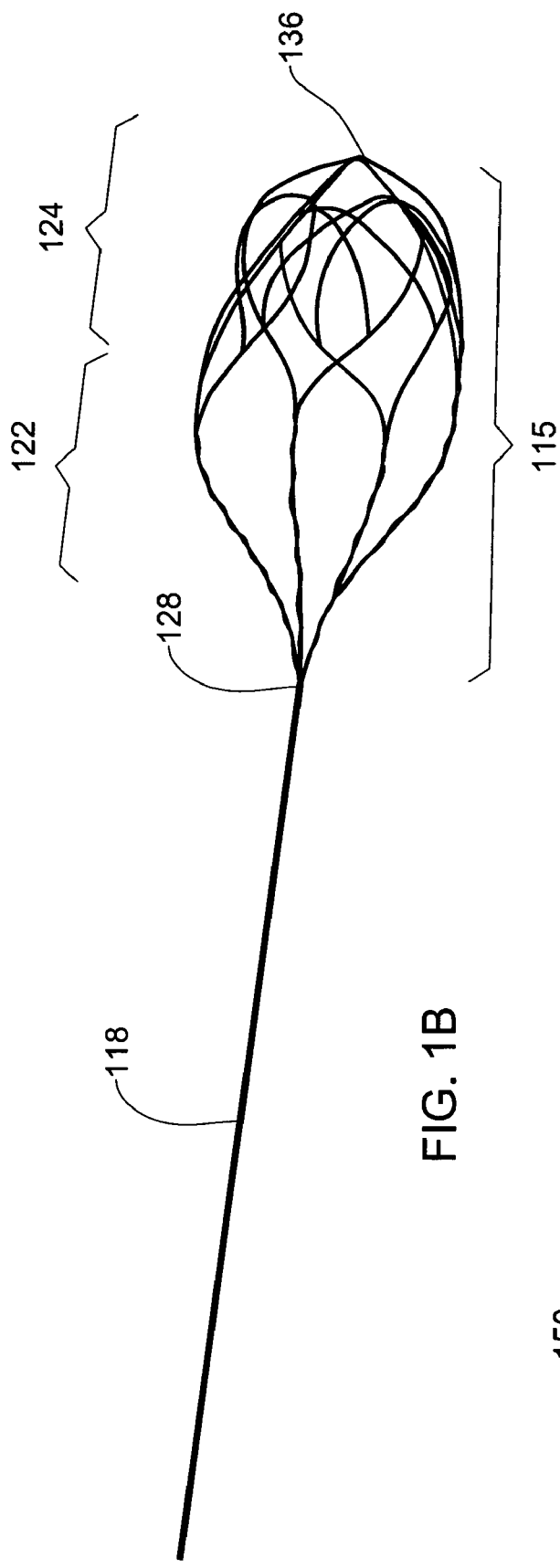
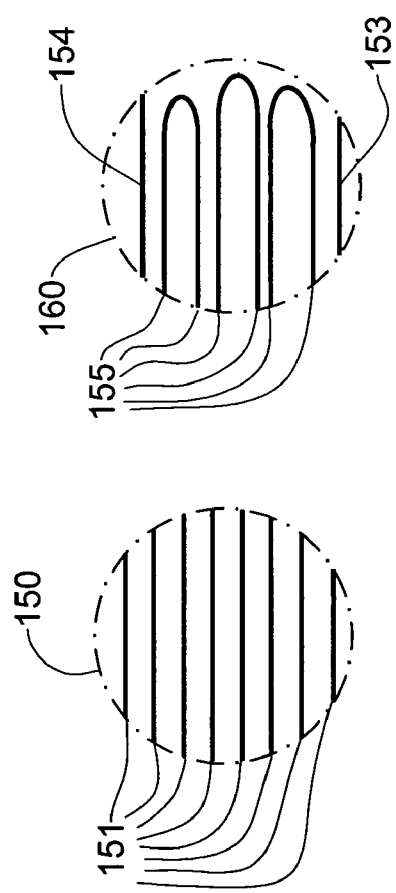
FIG. 1B
FIG. 1C

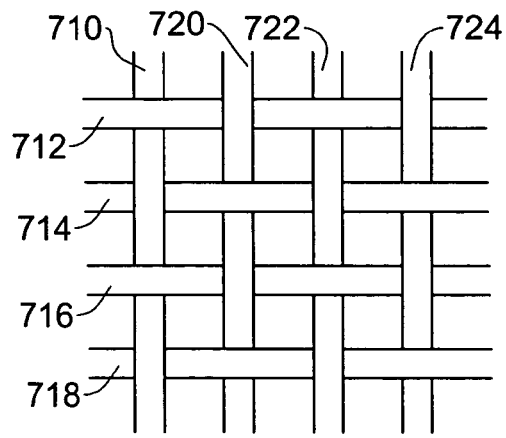
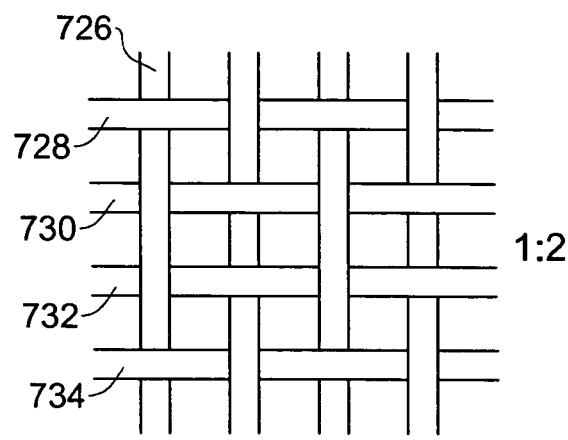
FIG. 12A
FIG. 12B
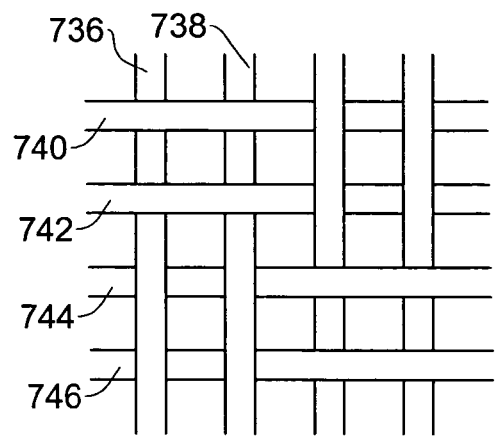
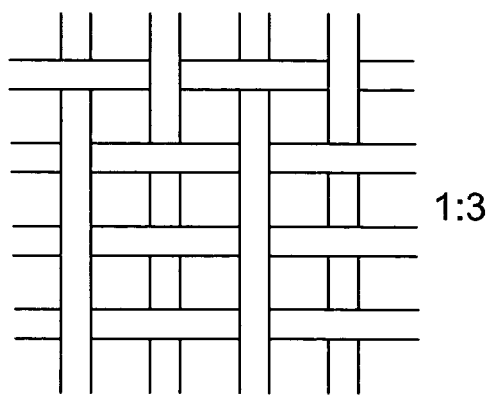
FIG. 12C
FIG. 12D
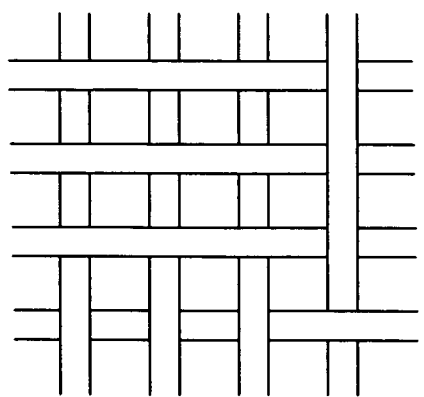
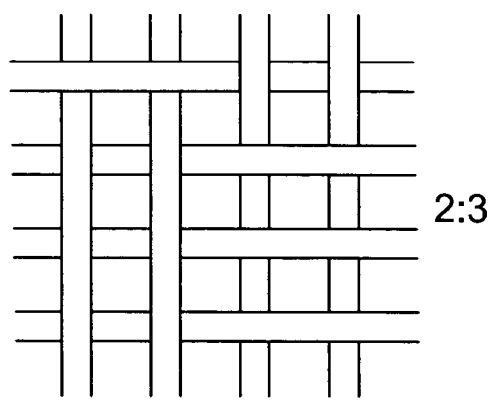
FIG. 12E
FIG. 12F

SURGICAL DEVICE FOR RETRIEVAL OF FOREIGN OBJECTS FROM A BODY

This is a continuation of parent application Ser. No. 10/216,672, filed Aug. 12, 2002.

FIELD OF THE INVENTION

This invention relates to a medical instrument for removing an object from a body, and in particular, to a surgical device for extracting calculi appearing in the biliary or urinary system.

BACKGROUND OF THE INVENTION

Despite the fact that by virtue of available modem video-assisted endoscopic instrumentation significant progress has been achieved in urological invasive treatment in general and in the extracting of foreign objects in particular, the evacuation of such objects like calculi from a surgical patient's body still remains a challenge for a surgeon.

In the course of complicated and time-consuming surgical treatment the removal of calculi of different sizes and characteristics from various sites along the urinary tract and from various locations within the body, (e.g. removal of gallstones and kidney stones) becomes essential. This challenge has resulted in the development of a variety of surgical tools for stone retrieval without the need for major surgery. The calculi retrieval tools, or so-called surgical extractors usually comprise a flexible tubular catheter formed as a tubular sheath adapted to penetrate along the body passages to reach the location of the object to be evacuated. A wire or cable is inserted within the catheter, which can be manipulated from the outside at the catheter's proximal end. The cable is connected to a basket deployed within the sheath at the catheter's distal end. The basket consists of flexible filaments made of either a memory shape material (e.g., stainless steel) or any other material capable of providing the basket with elasticity.

Depending on the manipulation, the basket may either retract inside the sheath to allow penetration of the catheter via passage or protract from the catheter. In the protracted position, the wires open due to the elasticity of their material and form a cage thus allowing the object to enter inside the basket through the open spaces left between its adjacent wires. Further retraction of the basket inside the sheath results in collapsing the cage and entrapping the object in the basket. Removal of the catheter will enable the whole device to be removed from the body organ together with the object immobilized within the basket.

It can be easily appreciated that the particular design of the basket-like element is crucial for entrapping and reliable retaining the object during evacuation.

Various attempts to devise the basket are known in the art. Examples of conventional baskets can be found in the web site www.bsci.com. According to the recent classification suggested by Boston Scientific Corporation, the currently employed baskets for stone retrieval can be broadly categorized into the following groups: (11) Flatwire baskets, (12) Helical baskets and (13) Multi-wire baskets.

An example of a flatwire basket is disclosed in U.S. Pat. No. 6,183,482. This basket comprises one or more legs to retrieve the calculi. At least one of the legs has an inner surface and an outer surface. The outer surface is curved to render the basket atraumatic. The inner surface can be flat such that the leg has a D-shaped cross-sectional configuration. It is reported in the literature that flatwire baskets minimize lateral basket wire movement and this facilitates and improves stone capture. Furthermore, flatwire baskets open reliably even in an undilated ureter. Flatwire baskets are available in a wide range of sizes and wire configurations. A method of manufacturing of such baskets is described, for example, in U.S. Pat. No. 5,658,296.

The intrinsic disadvantage of flatwire baskets is their unsuitability for capturing and immobilizing relatively small calculi, since the amount of wires in such baskets is limited to very few and the size of open space between the adjacent wires remains too large.

In an attempt to solve this problem and allow the capturing and retaining of small calculi, so-called helical baskets were devised. Examples of surgical extractors equipped with the helical baskets can be found in U.S. Pat. Nos. 3,496,330; 6,190,394; 4,347,846.

It is appreciated in the art that helical baskets incorporate strong, flexible wire construction in a spiraled shape design. The streamlined, spiraled shape is well suited for efficient, effective stone capture. As the basket is drawn back over the entrapped calculi, the configuration of the wires "sweeps" the stone into the basket.

U.S. Pat. No. 5,496,330 discloses a helical basket formed as a plurality of strands encased in a sheath and wrapped in a helical form. The displacement of a portion of the threads from the sheath causes their wide angular disposition to form a basket for retrieving the object. The threads include a plurality of individual filaments that are closely spaced through the length of the basket. By virtue of strands, formed as multiple, closely situated adjacent wires, the number of contact points with entrapped calculi is increased without requiring a concomitant increase in the size of the overlying sheath.

Nevertheless, one can appreciate that the above-mentioned advantage associated with the increased number of contact points may limit this basket to the treatment of small calculi and render this basket less suitable for the immobilization of relatively large calculi. The reason for this is the close angular disposition of the filaments that prevents the entry of large calculi in the limited open space between the adjacent filaments.

U.S. Pat. No. 6,190,394 discloses a medical retrieval basket formed as a plurality of flexible elements that are outwardly disposed to form a cage for entrapping objects therein. This basket was devised to enable the efficient entrapment of the objects and their reliable holding within the cage. To achieve this goal, the basket is manipulated by rotation and employs flexible elements having different sizes, different cross-sectional configuration and/or different spacing.

In one embodiment, the cage consists of non-twisted flexible elements as in flatwire basket design. In the other embodiment, the flexible elements are helically twisted. In both embodiments, the cage is symmetrical with respect to a plane drawn perpendicularly to the middle of the cage length.

It can be appreciated, however, that the above-mentioned intrinsic disadvantages associated with flatwire and helical baskets would be characteristic also to the basket disclosed in U.S. Pat. No. 6,190,394. The further disadvantage of the helical design is associated with the fact that parallel-directed helically shaped filaments are prone to entanglement.

U.S. Pat. No. 4,347,846 discloses a surgical extractor employing a cage or basket formed by steel wires and disposed in a helical path. Some of the wires follow a helix in clockwise direction, while other wires, in equal number, follow a helix in anti-clockwise direction. By virtue of this extractor, the reliability of retention of the body during evacuation is improved, since the body may enter within the extractor sheath when the cage is being retracted. This prevents the accidental escape of the body from the cage. Furthermore, by virtue of the opposite direction of the helically shaped filaments, any danger of their twisting and entanglement of the cage is avoided.

It should be emphasized that the general shape of the cage employed in the extractor described in U.S. Pat. No. 4,347, 846 is very similar to the shape of helical basket disclosed in U.S. Pat. No. 6,190,394. This shape is also symmetrical to a plane, drawn perpendicularly to the middle of the basket's length. Therefore, the same above-mentioned intrinsic disadvantages are characteristic to this helical basket as well. Furthermore, since the filaments are not bound together and only have points of passive contact in which they overlap, it can be appreciated that the cage will neither have sufficient radial rigidity to prevent escape of the calculi between adjacent filaments, nor sufficient dilatation ability to provide enough room between the entrapped calculi and the tissue of the passage. Thus, either the loss of calculi during evacuation or damage to the adjacent tissue might occur during the treatment.

In an attempt to overcome the disadvantages associated with the entrapment and retention of calculi of various sizes, a multi-wire parachute basket having two sections have been devised. In the first section, the amount of filaments is small and they are in spaced relationship to enable the easy passage of the calculi through the spaces between the filaments. The second section is formed as a plurality of filaments, extending from the filaments of the first section and defining a multi-wire cage. Since in this cage the filaments are in close relationship, it is possible to ensure more complete engagement of the captured calculi when the basket is in a protracted position and a more reliable grip when the basket is being retracted within the sheath.

One early attempt to devise a basket in accordance with the parachute concept is described in U.S. Pat. No. 3,472,230. This patent discloses a retrieval basket made of four spring wires connected to a slide. An umbrella made of suitable flexible web material is connected to the distal ends of the wires so that upon deployment of the basket the edges of the umbrella form a scraper. Retracting the basket is associated with scraping the debris from a body passage and its retaining within the umbrella.

The other example of the retrieval parachute basket, provided with web umbrella, is presented in U.S. Pat. No. 4,790,812. The disadvantage of the parachute baskets provided with the web umbrella is associated with difficulty in manufacturing and with the relatively large size of the web umbrella in the compacted condition.

The further progress in the design of parachute baskets have been achieved by devising multi-wire parachute baskets (see, for example, S.U. Pat. No. 1036325; R.U. Pat. No. 2022528, U.S. Pat. No. 6,168,603).

S.U. Pat. No. 1036325 describes a surgical extractor with multi-wire parachute basket formed with a first section, which is proximal to the sheath and with a second section, which is distal thereto. The proximal section comprises two separate branches extending from the sheath in a V-shaped fashion. The branches comprise strings that are woven from the individual wire filaments. From distal ends of the branches emerge individual wire filaments, which are bent as elongated elliptical loops. The loops emerging from the branches meet in a common point at the distal end of the extractor. Additional wire filaments are provided longitudinally extending within the loops. These filaments divide the loops into supplemental branches, which together define the second section of the basket.

The disadvantage of this basket is associated with the fact that it still does not always ensures reliable retention of the calculi, since the amount of branches along the basket is invariant and their filaments are parallel and separate. Thus, small calculi might escape through the room between the branches of the second section.

A similar construction of the multi-wire parachute basket is disclosed in U.S. Pat. No. 6,168,603. In this US patent is described surgical extractor on whose distal end is arranged a plurality of wires defining a retrieval basket. Each wire comprises a first portion having an individual strand and a second portion comprising a plurality of filaments. When a retaining sheath of the extractor is retracted the wires formed of a shape memory material expand. Each strand assumes a spaced relationship to define a first section of the basket. A plurality of filaments define a second section of the basket. Widely spaced wires of the first section promote capturing the object and closely spaced wires of the second section enable retention of the captured object. It is worth mentioning that in one of the embodiments the second section is formed from filaments which are helically wound and angularly spaced.

R.U. Pat. No. 2022528 discloses a surgical extractor provided with a basket formed from at least two branches made of metallic strings. The main branches define the first section of the basket, which is intended for entering the calculus within the basket. Each branch forms at its distal end sub-branches, which are made of two main sub-branch and one auxiliary sub-branch. The sub branches define the second section of the basket. The sub-branches and the auxiliary branches have different thicknesses and different elasticities. By virtue of this basket, the reliability of entrapment and immobilization of the entrapped calculus is improved, since its construction allows for the variation of the amount and arrangement of the sub-branches.

However, the above mentioned multi-wire parachute baskets only partially solve the problem of reliable capturing, immobilization and holding of calculi, irrespective of their size. The reason for this is the size of the open space along the branches, which is equal to the length of filaments of the second section. Calculi whose size is shorter than this length can easily escape from the basket. Furthermore, in the above baskets the filaments of neighboring branches are either fully separate (as in S.U. Pat. No. 1036325) or only passively overlap (as in U.S. Pat. No. 6,168,603 and R.U. Pat. No. 2022528) and they are not entwined. By virtue of this provision the radial rigidity of the cage is very limited and might be not sufficient to prevent the possibility of the adjacent filaments being spread apart by the calculus during entrapment, and the calculus thus escaping. Insufficient radial rigidity is associated also with the possibility of damaging adjacent body tissues by the entrapped calculus protruding through the open space formed by the spread filaments. The insufficient radial rigidity deteriorates the dilatation ability of the whole basket and therefore contributes to the possibility of damage occurring to the nearby body tissues.

SUMMARY OF THE INVENTION

Despite the extensive prior art in the area of surgical devices employing retrieval baskets for extracting objects from a body, there is still a need in the art for, and it would be useful to have a novel, convenient and safe surgical tool suitable for the reliable and efficient extraction of foreign objects from the body irrespective of the size of the object and its location within the body.

It would also be advantageous to have a novel surgical tool, provided with a retrieval basket defined by increased structural rigidity and dilatation ability, thus reducing the probability of traumatizing adjacent body tissues.

It would still be advantageous to have a novel and improved surgical tool defined by easy and fast protracting and retracting from the sheath and thus enabling more reliable functioning during the surgical treatment.

It would yet be advantageous to have a novel and improved surgical tool ensuring the adaptation to elastic properties of the surrounding body tissues.

The aforementioned needs and advantages of the present invention can be achieved in accordance with the following combination of its essential features, referring to different embodiments thereof as a surgical device and as a retrieval basket.

According to one embodiment of the invention, there is provided a novel surgical device for extracting objects from a body including a retrieval basket and a basket control assembly.

The retrieval basket is suitable for entrapping the object and retaining it during extraction. The basket comprises a structure having a proximal end and a distal end. The structure is formed by a plurality of filaments fabricated from a single or several wires. It should be noted that the wires selected for the construction of the basket can be single-filament wires, or, when desired, can be multi-filament wires.

The filaments extend between the proximal end and the distal end. At least a part of the filaments, which originate from the proximal end, can arrive at the proximal end after winding. At least a part of the filaments are configured in the form of loops. At least a part of the loops are interlaced so as to define a net at the distal end, and thereby impart structural rigidity and dilatation ability to the basket when opened.

According to one embodiment of the invention, the size of holes (cells) of the net decreases from the proximal end towards the distal end. In other words, the density of the net increases from the proximal end to the distal end of the structure.

According to one embodiment of the invention, the filaments in a region of the structure at the proximal end form at least two strands, each including a plurality of the filaments. According to this embodiment, the structure of the basket has a parachute-like shape, i.e., a form of the basket is symmetrical along the basket central axis.

According to another embodiment of the invention, the filaments in a region of the structure at the proximal end form a plurality of strands and one of the strands is common for all the filaments. The structure of the basket, according to this embodiment, has a spoon-like shape.

The basket control assembly is suitable for bringing the basket to the object and is adapted for manipulating the basket. The basket control assembly includes a catheter in the form of a tubular sheath to be inserted within the body. The catheter is suitable either for retracting the basket within the sheath, to enable bringing the catheter within the body, or for protracting the basket from the sheath to enable opening of the basket.

According to one embodiment of the invention, the filaments are made of metallic material. The metallic material can be selected from NiTi based alloy, (e.g., Nitinol) and stainless steel.

According to another embodiment of the invention, the filaments are made Of non-metallic material, e.g. Capron (polyamide resin).

According to yet another embodiment of the invention the filaments are made of a material that has thermo-mechanical shape memory characteristic. The surgical device, according to this embodiment, comprises a controllable power supply source coupled to the filaments for passing an electric current therethrough. This electric current should be capable of heating filaments and thereby cause the filaments to change their shape due to the heating. The filaments of the basket can be covered by an insulating layer. The insulating layer can, for example, be made of Teflon (polytetrafluoroethylene).

The surgical device of the present invention has many of the advantages of the aforementioned techniques, while simultaneously overcoming some of the disadvantages normally associated therewith.

For example, since the basket of the present invention has an asymmetric net shape, the proximal net holes are bigger than the distal net holes. This shape ensures easy stone capture (through the distal end), and on the other hand, ensures foolproof extraction without loss of the stone (through the proximal end).

The structure of the basket of the stone extractor allows to increase their springiness and flexibility that, in turn, allows to decrease their traumatic influence on the organ. Such an effect is, inter alia, achieved by the manner in which the NiTi wires are twisted and interlaced. Such superelasticity allows to treat the organ better in the case of small stones, thus, e.g., minimize the damage of the urinary tract tissue.

The surgical device according to the present invention may be easily and efficiently manufactured and marketed.

The surgical device according to the present invention is of durable and reliable construction.

The surgical device according to the present invention may have a low manufacturing cost.

Thus, in accordance with one broad aspect of the invention, there is provided a retrieval basket for entrapping and retaining an object located in a body for its extraction therefrom, the basket comprising a structure having a proximal end and a distal end, and constituted by a plurality of filaments extending from the proximal end towards the distal end and being in the form of loops, characterized in that at least a part of the loops are interlaced so as to define a net at least at the distal end, thereby imparting structural rigidity and dilatation abilities to the basket when opened.

In accordance with another one broad aspect of the invention, there is provided a surgical device for removing a foreign object from a body, comprising:

a retrieval basket for entrapping and retaining an object located in a body for its extraction therefrom, the basket comprising a structure having a proximal end and a distal end and constituted by a plurality of filaments extending from the proximal end towards the distal end and being in the form of loops;

at least a part of the loops are interlaced so as to define a net at least at the distal end, thereby imparting structural rigidity and dilatation abilities to the basket when opened; and a basket control assembly coupled to the basket, comprising a tubular sheath adapted to penetrate into the body for reaching the object, and a manipulator for manipulating the basket for extraction the object from the body, the assembly is configured for retracting the basket within the sheath and protracting the basket therefrom for its opening.

There has thus been outlined, rather broadly, the more important features of the invention in order that the detailed description thereof that follows hereinafter may be better understood. Additional details and advantages of the invention will be set forth in the detailed description, and in part will be appreciated from the description, or may be learned by practice of the invention.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 1B illustrates an example of a basket in which the filaments form a pushing cable.

FIG. 1C illustrates two examples of the cross-section (A-A in FIG. 1A) of the basket woven from a single length of wire or from several wires.

FIGS. 12A-12F illustrate schematically examples of how distal ends of the loops are intertwined.

DETAILED DESCRIPTION OF THE INVENTION

The principles and operation of the surgical device according to the present invention may be better understood with reference to the drawings and the accompanying description, it being understood that these drawings and examples in the description are given for illustrative purposes only and are not meant to be limiting.

Figure 1A:
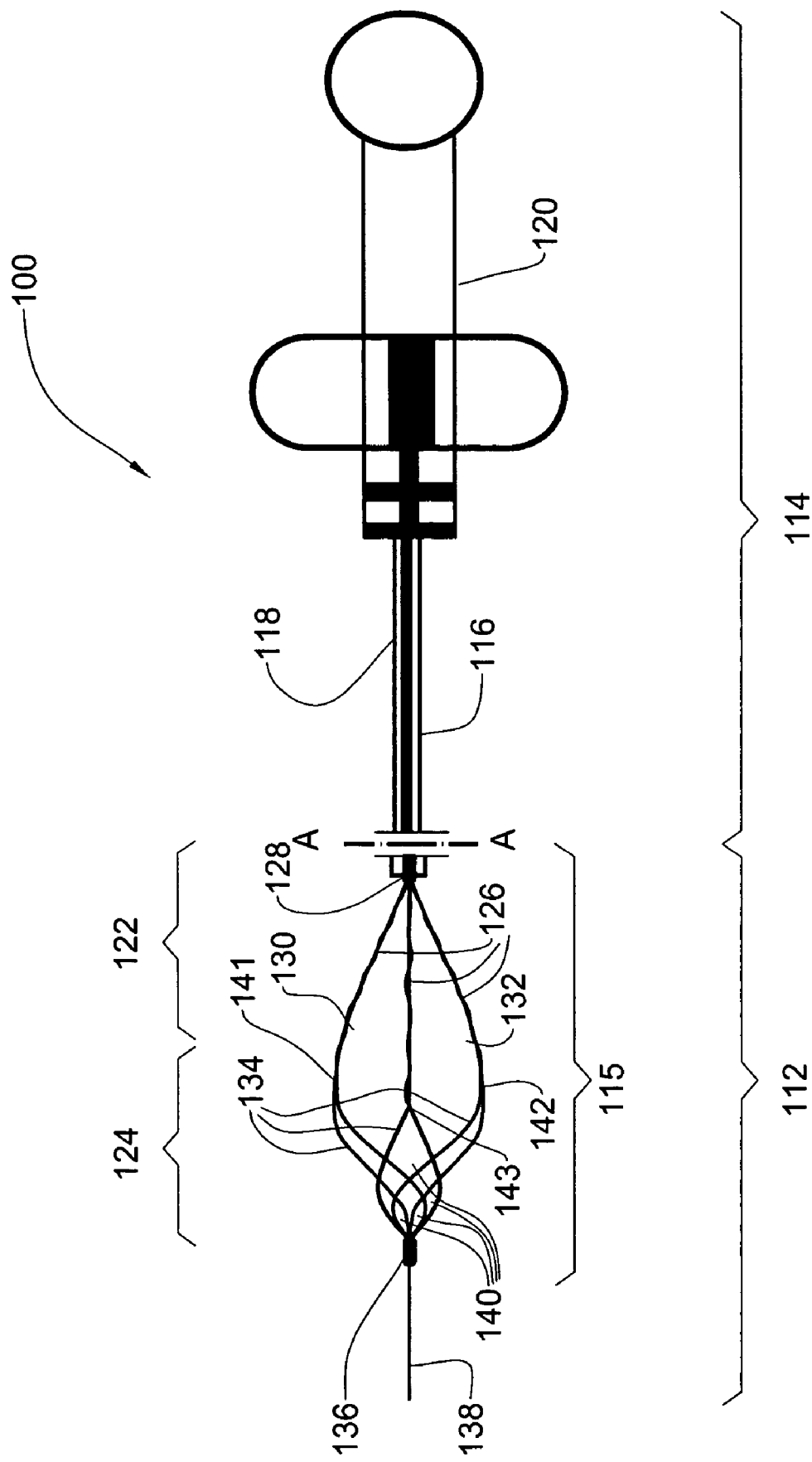
FIG. 1A is a schematic view of a longitudinal cross-section of a surgical device, according to one embodiment of the preset invention.

Referring to FIG. 1A, a general schematic view of a surgical device 100 devised for the retrieval of various calculi or other objects from a human or animal body during the treatment of biliary, urinary or other systems is shown, according to one embodiment of the invention. Such treatment may include the extraction of stones from the urethra (e.g., cystic calculus and ureteral calculus), as well as bile duct (choledochal) stone, biliary calculus, etc. It should be appreciated that the device 100 can also be used in other surgical treatments in combination with other surgical instruments and equipment, (e.g. for the destruction of calculi, etc.).

The device 100 of the invention comprises a retrieval basket portion 112 and a control means portion 114. The retrieval basket portion 112 is suitable, inter alia, for the immobilization of the object to be evacuated and its retention during extraction. The control means portion 114 is suitable for manipulating the retrieval basket portion 112.

The control means portion 114 includes a flexible tubular catheter 116, configured as a sheath, adapted to penetrate along the body passages near the location of the object (not shown) and a manipulator 120.

The retrieval basket portion 112 includes a retrieval basket 115 that is coupled to a pushing element 118 (e.g., rod, cable or wire), for example, via a connector (not shown). The pushing element 118 is arranged within the catheter and connected to the manipulator 120.

In practice, a surgeon can manipulate the pushing element 118 by virtue of the manipulator 120, and thus the basket 115 can be either retracted within the catheter 116 or protracted therefrom. The surgeon, by holding the manipulator 120, can also maneuver the catheter 116 within the body organ (not shown), (e.g. to displace it by turning, pushing or pulling).

In practice, the surgeon moves the catheter behind the object to be extracted, and then protracts the retrieval basket portion 112 from the catheter 116. Once the basket 115 is protracted it opens due to its resiliency and is ready for receiving the object to be entrapped therein. The surgeon pulls the pushing element 118 together with the retrieval basket portion 112 until the basket 115 entraps the object, and thus extracts the entrapped object from the body.

The retrieval basket 115 comprises a structure having a proximal end 128 and a distal end 136 and is formed by a plurality of filaments fabricated from a single length of wire or several wires. The filaments extend from the proximal end 128 towards the distal end 136.

As was noted above, the filaments of the retrieval basket 115 can be coupled to the pushing element 118 that is provided as a separate unit at the proximal end 128. Alternatively, the filaments can be bound together (e.g., glued, soldered, weld, etc.) at the proximal end 128 and extended towards the manipulator. In such a case the filaments bound together form the pushing element 118. An example of such a configuration is shown in FIG. 1B.

Referring to FIG. 1C, two examples of cross-section (A-A in FIG. 1A ) of the basket near the proximal end 128 are illustrated.

According to the first example, a cross-section 150 is formed of filaments 151 woven from a single length of wire or from several wires that enter into the cross-section from the left side and leave the cross-section in a whole number from the right side. These filaments 151 themselves can form a pushing cable (118 in FIG. 1A).

According to the second example, a cross-section 160 is formed of filaments woven from a single length of wire among which only filaments 153 and 154 enter into the cross-section 150 from the left side and leave the cross-section from the right side, whereas filaments 155 enter into the cross-section 160 from the left side, turn around and leave the cross-section also from the left side. The basket utilizing this configuration of the filaments can be coupled to the pushing element 118 (provided as a separate unit) at the right end of the cross-section 160. For this configuration, the filaments 153 and 154 can be arranged within the catheter 116, coupled to the manipulator 120 and used for extraction of the basket from the body in case of emergency, e.g., when the pushing element is torn off from the basket.

Turning back to FIG. 1A, the basket 115 can be divided into a first section 122, which is proximal to the control means portion 114, and a second section 124, which is distal thereto. According to the embodiment shown in FIG. 1A, in the first section 122 the filaments form strands 126 arranged in branches. Hereinafter, the terms "strands" and "branches" in the context of this description are used interchangeably. The filaments in the strands 126 are entwined and spatially arranged in such manners that upon protracting from the catheter 116 (sheath) they can be readily spread out. The filaments meet in the proximal end 128, where the retrieval basket 115 is connected to the pushing element 118.

In the second section 124 the strands ramify at branching points 141, 142, 143 and form loops 134. At least a part of the loops 134 are interlaced so as to define a net forming a shape of the structure near the distal end 136. It should be appreciated that the net formed thereby has a hole (cell) size decreasing from the proximal end towards the distal end. The net formed thereby imparts structural rigidity and dilatation ability to the basket when it is opened.

In the open condition, the first section 122 of the basket 115 has relatively large open spaces 130 and 132 left between the adjacent branches. It can be easily appreciated that by virtue of the open spaces 130 and 132, the immobilization of the object and receiving thereof inside the first section 122 becomes easy and convenient during the first stage of the treatment, when the surgeon begins pulling the basket 115 for entrapping the object.

In the embodiment of the invention shown in FIG. 1A, the strands are arranged in three branches and define the first section 122 of the basket 115. It should be appreciated that in practice only two branches might be sufficient to define the first section 122.

According to one embodiment of the invention, the loops 134 are configured from the same wire filaments from which the branches are entwined. It is possible however that the loops are made of separate wire filaments and connected to the respective branches, e.g. by soldering.

According to one embodiment of the invention, the most distal ends of the loops 134 are bound together (e.g., by a bushing) at the distal end 136 to form a tip. It should be appreciated that when desired, after the tip, the wire filaments can be intertwined to form a guiding rod 138. The guiding rod 138 can function as a guide to facilitate the displacement of the retrieval basket portion 112 as well as to facilitate the penetration and movement of the whole surgical device 100 within the body organs.

As was noted above, at least a part of the loops 134 are overlapped and interlaced. The overlapped and interlaced wire filaments define collectively the second section 124 of the basket 115. It should be appreciated by a person versed in the art that the interlaced loops intertwine one with another. At least a part of the filaments, which originate from the proximal end 128, can arrive at the proximal end after winding. By virtue of this arrangement, the second section 124 of the basket 115 is configured as a net, having a cell structure with relatively small cells 140, suitable to retain relatively small objects reliably entrapped therein.

According to one embodiment of the invention, the size of the cells of the net decreases towards the distal end 136. In other words, a density of the net increases from the proximal end 128 to the distal end 136 of the structure.

It has been empirically revealed that this net structure has improved radial rigidity and dilatation ability, thus rendering the whole basket to be less traumatic.

The retention ability of the basket depends on the size and shape of the cells, which, in turn, can be controlled by the size of the loops, their amount and spatial arrangement of their distal ends. These features of the invention will be described and illustrated below with reference to further drawings. Furthermore, although it is not shown specifically in the drawings it should be understood that in accordance with the invention the amount of loops emerging from each branch can be similar or dissimilar, and so their size.

It should be appreciated that the strands and loops can be configured from filaments made of metallic or non-metallic (e.g., plastic) material having sufficient elasticity to enable opening the basket when it is protracted from the sheath. This material should be also biologically inert. Example of the materials appropriate for the filaments include, but are not limited to, stainless steel, superelastic TiNi alloy and Capron. It is also recommendable to coat metallic wire filaments by an inert coating, e.g. Teflon.

Referring to FIGS. 2A-2D, various projections of the configuration of a retrieval basket 200, in accordance with another embodiment of the invention, will be described in more detail. In this embodiment, which in general is similar to the embodiment shown in FIG. 1A, only two strands 202, 204 define the first section of the basket 200 and thus a relatively large open space is available between the branches enabling easy immobilization of large calculi. The strand 202 ramifies at branching points 220 and 221 and provides a respective couple of loops 206, 208. In a similar manner, the strand 204 ramifies at branching points 230 and 231 and provides a respective couple of loops 210, 212. The loop 206 is less than the loop 208, and the loop 210 is less than the loop 212. These loops overlap and interlace in several points. For the sake of simplicity, only two points, namely 214 and 216 are designated in FIG. 2B to show the interlacement of the wires, from which the loops 210 and 206, respectively, are configured.

Figure 2A:
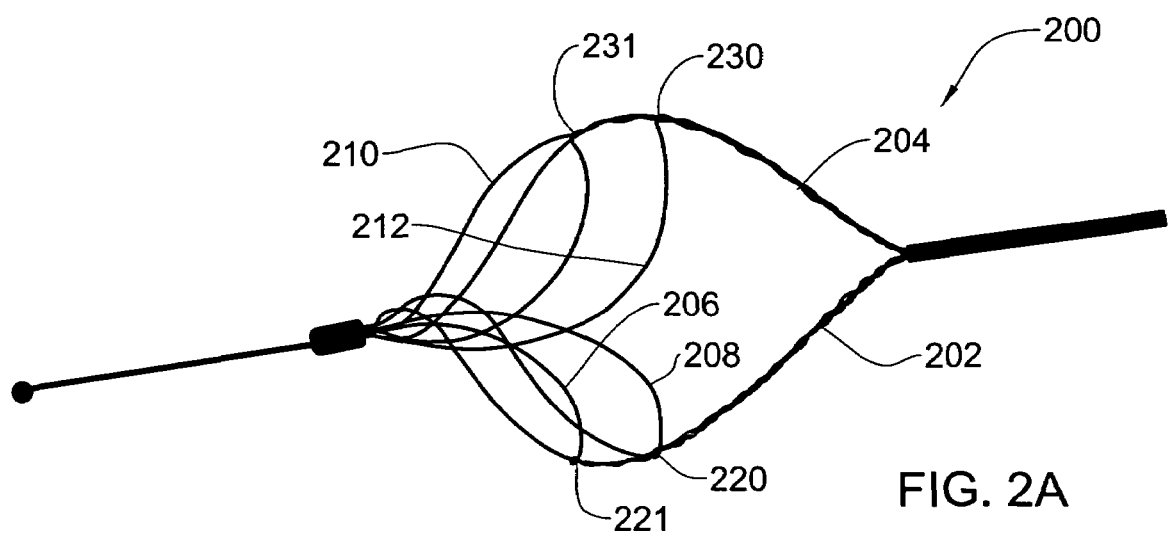
FIGS. 2A-2D illustrate various views of the basket provided with two branches, according to one embodiment of the invention.
Figure 2B:
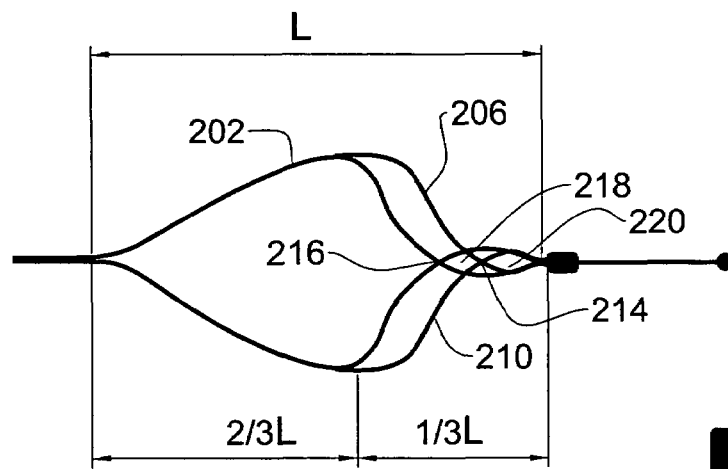
Figure 2C:
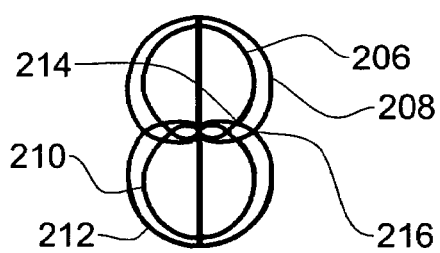
Figure 2D:
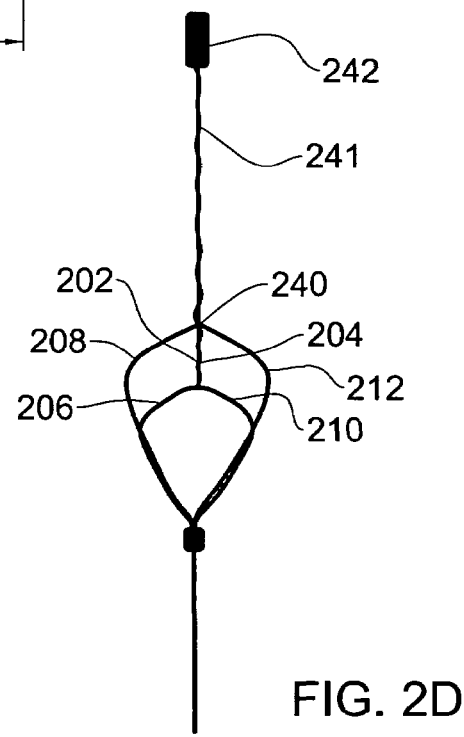

It can be appreciated that by virtue of this spatial arrangement a net-like structure is formed, consisting of small cells, two of which are designated in FIG. 2B by numerals 218 and 220. It should be appreciated that by virtue of loops having dissimilar size it is possible to form additional cells without introducing new branches.

It should be understood that since the wire filaments (from which the loops are made) are interlaced, an additional structural rigidity to the net-like structure is submitted. Hence, by virtue of this configuration, very reliable retention of the entrapped object (e.g., calculi) is ensured when it is extracted from the body.

According to this embodiment of the invention, the retrieval basket 200 has a first section, defined by strands 202, 204, and a second section, defined by loops 206, 208, 210, 212, forming net cells. For example, the length of the first section can be about ⅔ of the total basket length, i.e., the length of the second section can be about ⅓ of the total length. This relationship of the length is schematically shown in FIG. 2B, where the symbol L designates the total basket length.

The strands 202 and 204 are bound together at a basket proximal end 240 to form a cable 241. The cable 241 is coupled to a pushing element 242 (see FIG. 2D) to extend the length of the cable 241.

Figure 3A:
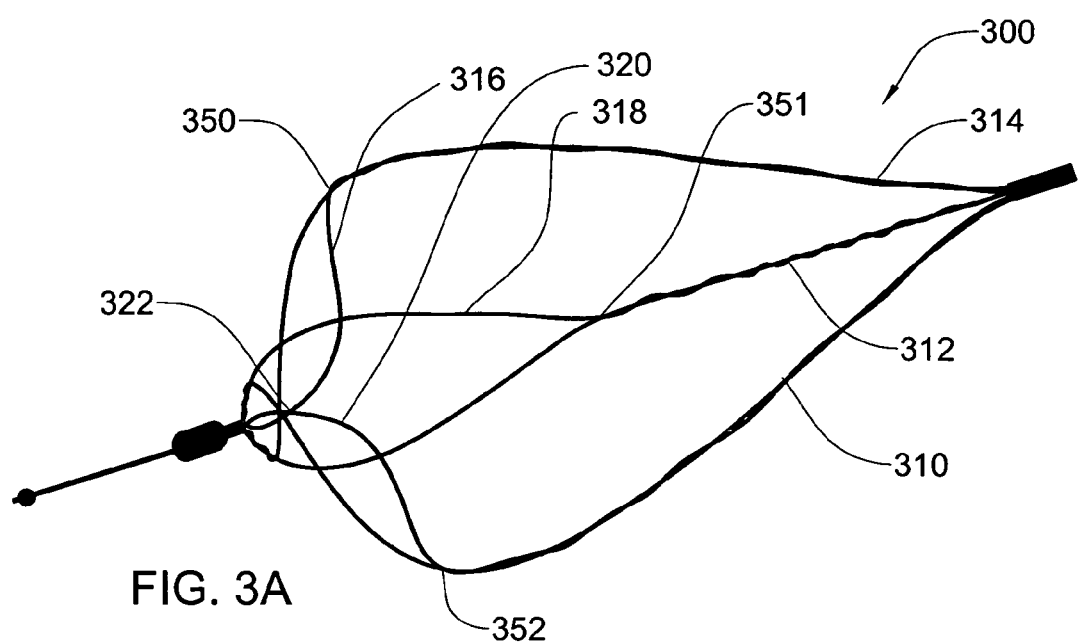
FIGS. 3A-3D illustrate various views of the basket provided with three branches, according to another embodiment of the invention.
Figure 3B:
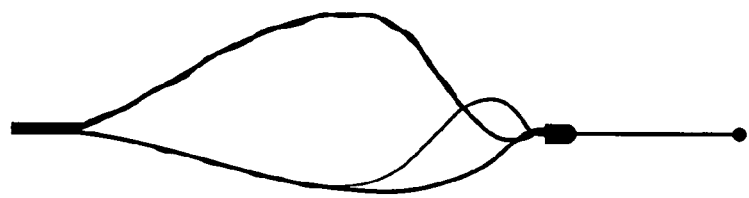
Figure 3D:
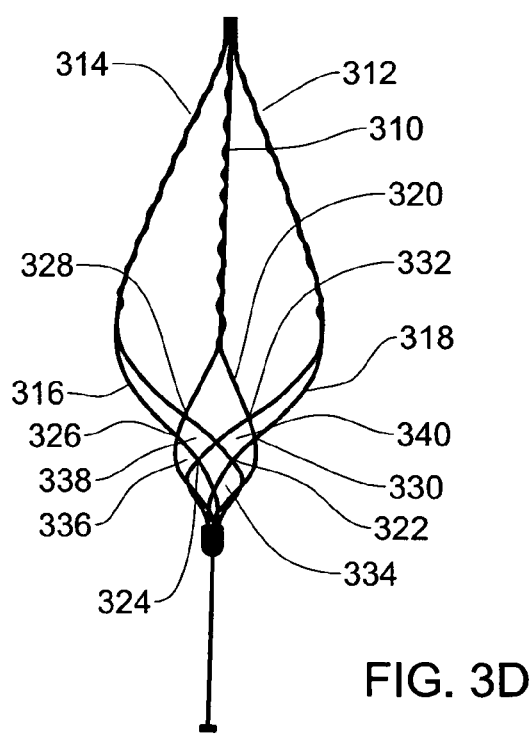
Figure 3C:
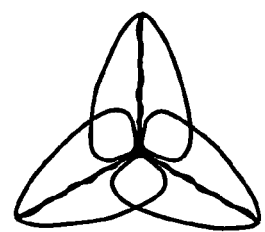

Another embodiment of the invention is illustrated in FIGS. 3A-3D. Here, three similar strands 310, 312, 314 define the first section of a basket 300. The strands 310, 312, 314 ramify at branching points 350, 351, 352 and provide loops 316, 318, 320, emerging from the branching points 350, 351, 352. The loops spatially overlap and interlace in several points. As can be seen in FIG. 3D, the loops 316 and 318 interlace in points 322 and 324, the loops 320 and 316 interlace in points 326, 328 and the loops 320, 318 interlace in points 330, 332. By virtue of this provision, a net-like structure is formed including several cells, some of which are designated in FIG. 3D by numerals 334, 336, 338, 340. The loops and cells collectively define second section of the basket 300, in which the entrapped object can be reliably retained during extraction. Similarly to the previous embodiment, since at least some of the individual wire filaments, from which the loops are made are interlaced, a net-shaped structure is formed, thereby imparting improved rigidity to the basket structure.

Figure 4A:
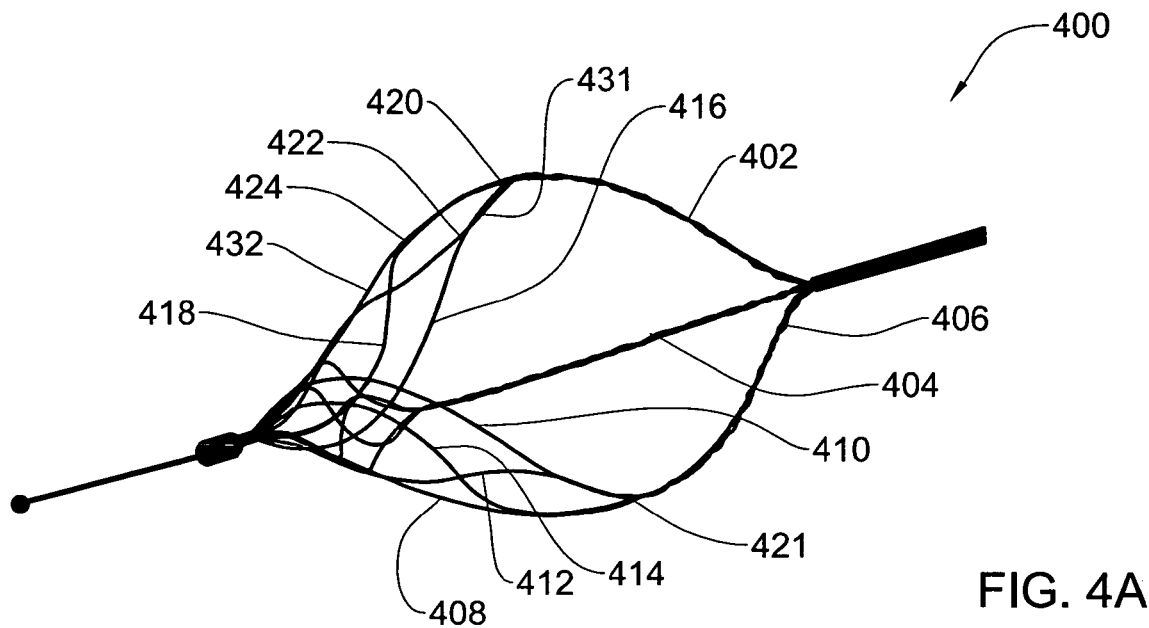
FIGS. 4A-4D illustrate various views of the basket provided with three branches, each of which is configured with two loops, according to still another embodiment of the preset invention.
Figure 4B:
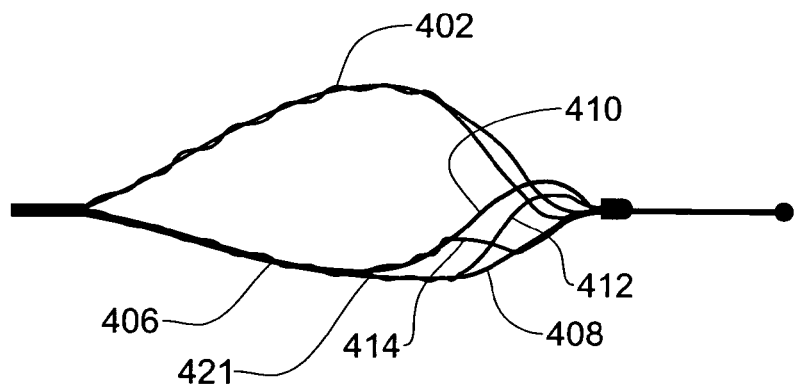
Figure 4D:
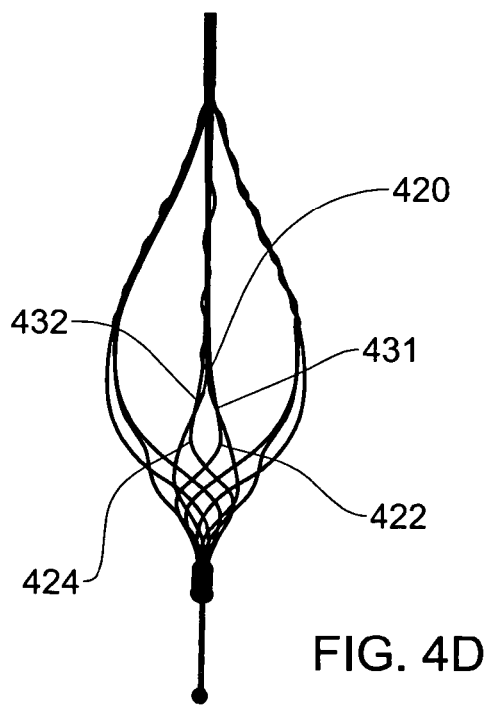
Figure 4C:
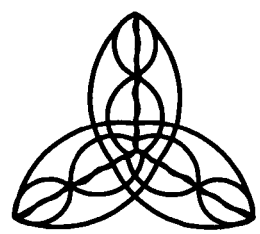

Referring now to FIGS. 4A-4C, still another embodiment of the retrieval basket is illustrated. According to this embodiment, a retrieval basket 400 includes three strands 402, 404, 406. Each branch is made of four entwined wire filaments. The branches 402, 404, 406 ramify at branching points and provide interlaced loops. For example, the strand 402 ramifies at a branching point 420 into strands 431 and 432. In turn, the strands 431 and 432 ramify at the branching points 422 and 424 and thus for loops 416 and 418, respectively. One of the loops (e.g., the loop 416) has a regular shape, while the other loop (e.g., the loop 418) is twisted and has an 8-shape configuration.

According to another example, as seen in FIGS. 4A and 4B, the wire filaments 408, 410, 412, 414 emerge from a branching point 421 of the strand 406. The filaments 408 and 410 form regular loop, while the two other filaments 412 and 414 are twisted and form an 8-shaped loop.

The wire filaments are overlapped and some of the loops are interlaced and form a net. It is seen, for example in FIG. 4A, that the filament 410 of the loop referring to the strand 406 interlaces with the filaments 416, 418 of two loops emerging from strand 402. By the same token, the filament 416 of the loop referring to the strand 402 interlaces with the wire filaments 410 and 412 of the loop emerging from the strand 406.

It can be readily appreciated that by virtue of this arrangement the whole second section of the basket becomes a net, having a densely meshed structure since twisted loops also contribute to the formation of cells. The cells formed by the intersection of the distal ends and the cells formed due to twisting collectively define the net-shaped structure, which is especially suitable for reliable retention of small objects or calculi. At the same time, sufficient space is still reserved between the branches to allow easy entrapment of relatively large objects or calculi.

Figure 5A:
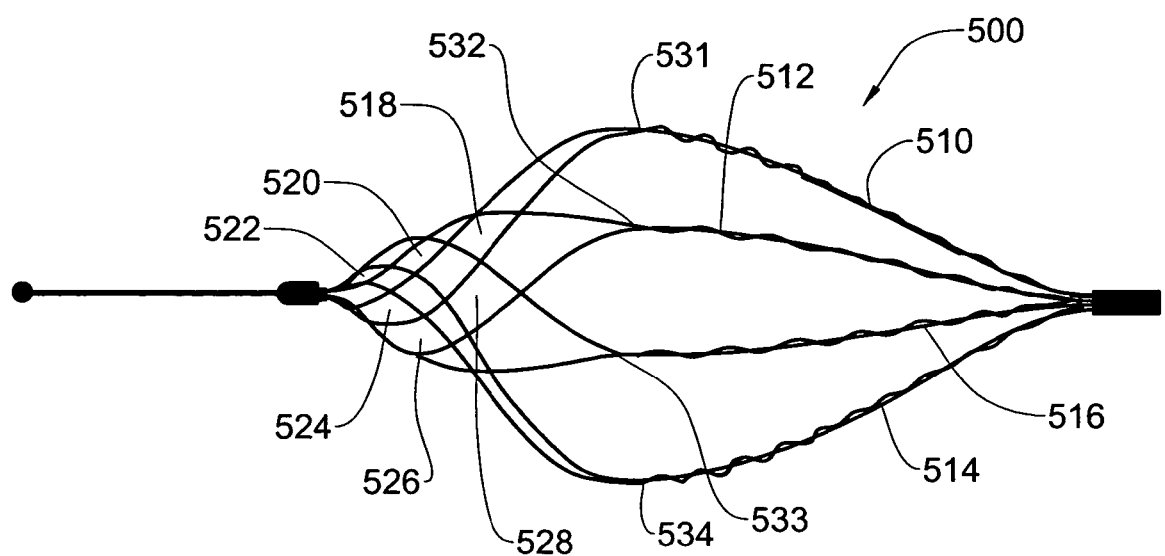
FIGS. 5A-5D illustrate various views of the basket provided with four branches, each of which is equipped with one loop, according to yet another embodiment of the preset invention.
Figure 5B:
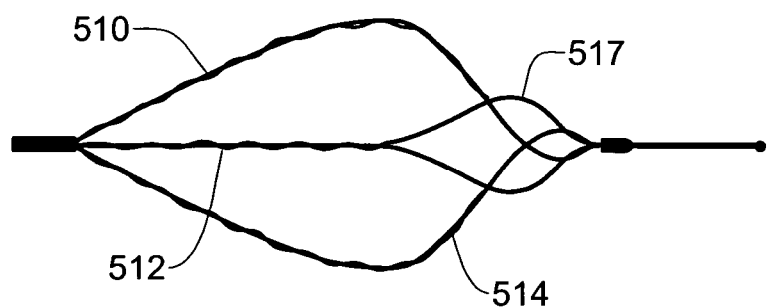
Figure 5D:
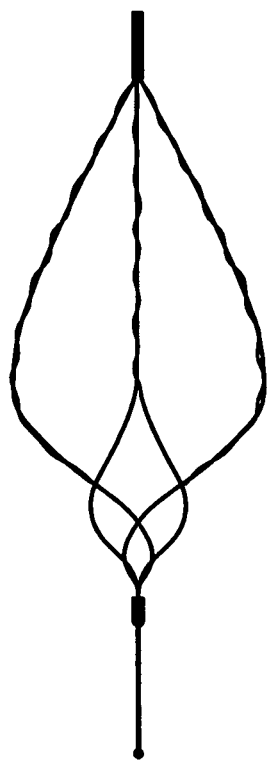
Figure 5C:
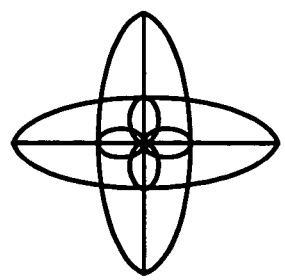

Referring to FIGS. 5A-5D, yet another embodiment of the invention is illustrated. As can be seen in FIG. 5A, a basket 500 has a first section, defined by four strands 510, 512, 514 and 516. Each strand is provided at the distal end thereof (i.e. at branching points 531, 532, 533, 534) with a corresponding loop, each loop having an elongated shape. One such loop emerging from the strand 512 is designated in FIG. 5B by a numeral 517. Distal ends of the loops are interlaced with the formation of a plurality of small cells. Some of the cells are designated by numerals 518, 520, 522, 524, 526, 528. The cells together with the loops define spatially a second section of the basket 500. It should be understood that similarly to the previous embodiments, since the loops are interlaced, such a net-shaped structure renders the resulting structure additional structural rigidity.

Figure 6A:
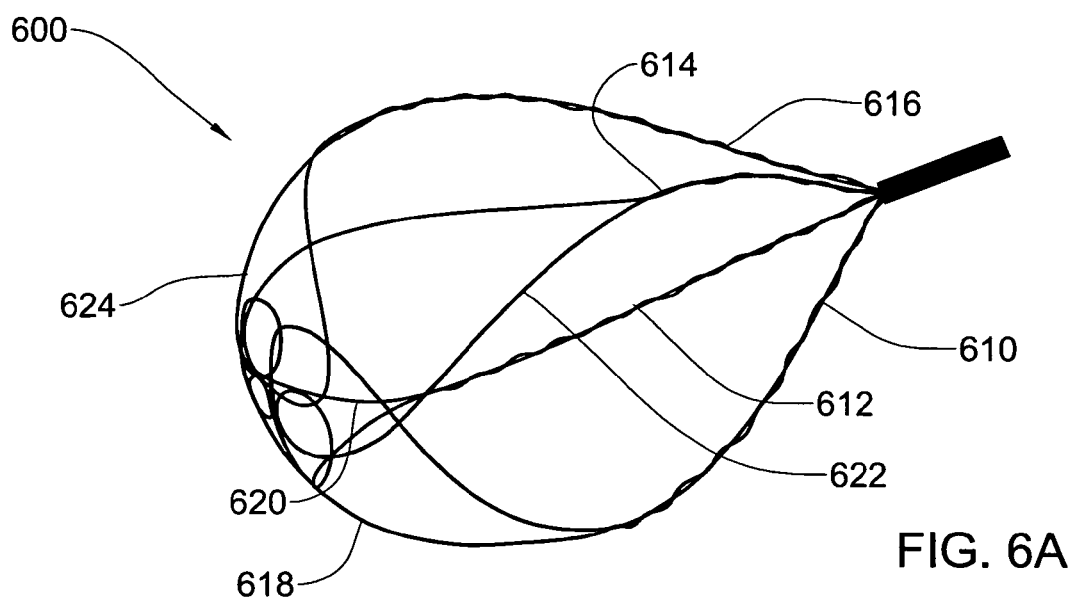
FIGS. 6A-6E illustrate various views of the basket shown in FIGS. 5A-5D in which the loops are configured in an 8-like fashion, according to one embodiment of the preset invention.
Figure 6C:
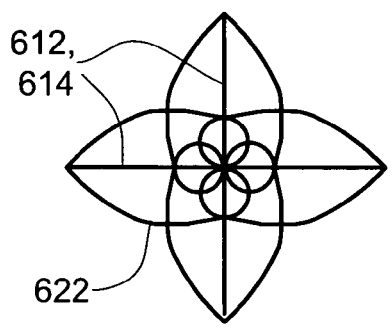
Figure 6B:
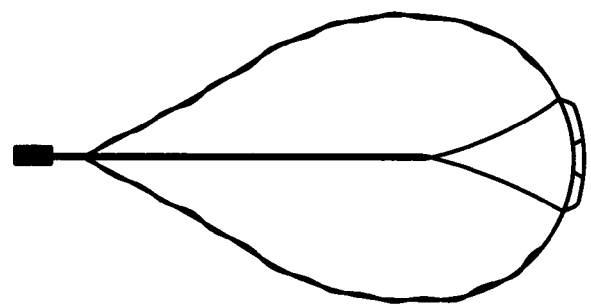
Figure 6D:
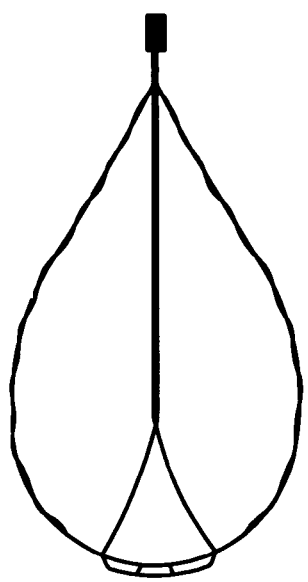
Figure 6E:
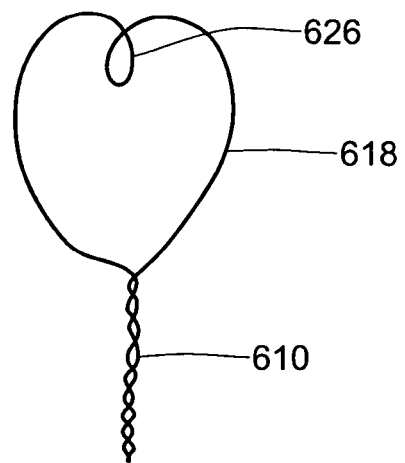

Referring to FIGS. 6A-6E, still a further embodiment of the invention is shown. Accordingly, four strands 610, 612, 614, 616, which at the distal ends thereof with corresponding loops 618, 620, 622, 624, form a basket 600. The loops 618, 620, 622, 624 are provided with dissimilar shapes. Furthermore, the loops are bent in such a manner that additional small loops are formed at the distal end of each loop. FIG. 6E shows one such loop 618 that emerges from the strand 610 and terminates at the place from which an additional small loop 626 emerges. For example, the additional loops are provided with a circular shape and they overlap and interlace, thus defining the dense net-like structure of the second section of the basket.

It can be readily appreciated that by providing the loops with various shapes it is possible to vary also the size and shape of the cells, formed at the intersection of the loops, thus control the retention ability of the basket.

Figure 7A:
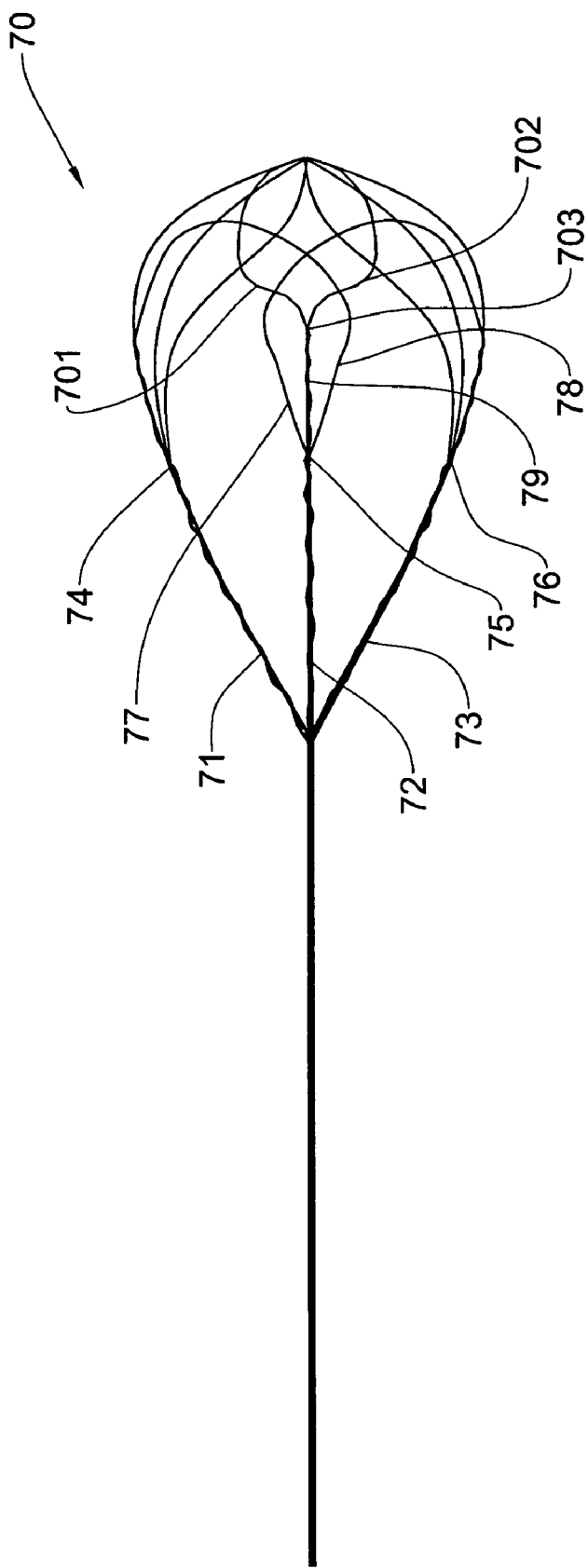
FIGS. 7A and 7B are plan and top schematic views of a longitudinal cross-section, respectively, of a basket according to still further embodiment of the invention.
Figure 7B:
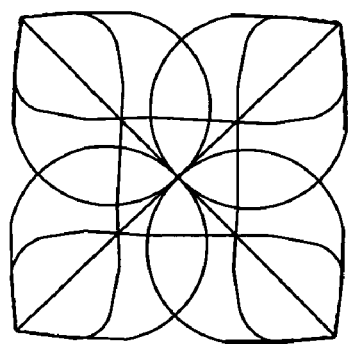

Referring now to FIGS. 7A and 7B, still a further embodiment of the invention is illustrated. According to this embodiment, a retrieval basket 70 includes four strands configured in branches. Only three such strands 71, 72 and 73 can be seen in FIG. 7. Each strand is formed of four entwined wire filaments. These strands ramify at branching points 74, 75, 76 and result in interlaced loops. For example, the strand 72 ramifies at the branching point 75. The filaments 77 and 78 that emerge from the branching point 75, form two corresponding loops. A branch 79 consisting of two remaining entwined filaments also emerges from the branching point 75. The branch 79 ramifies at a branching point 703 and provides a loop formed of the filaments 701 and 702. According to this embodiment of the invention, the loops formed thereby are interlaced so as to form a net structure.

Figure 8A:
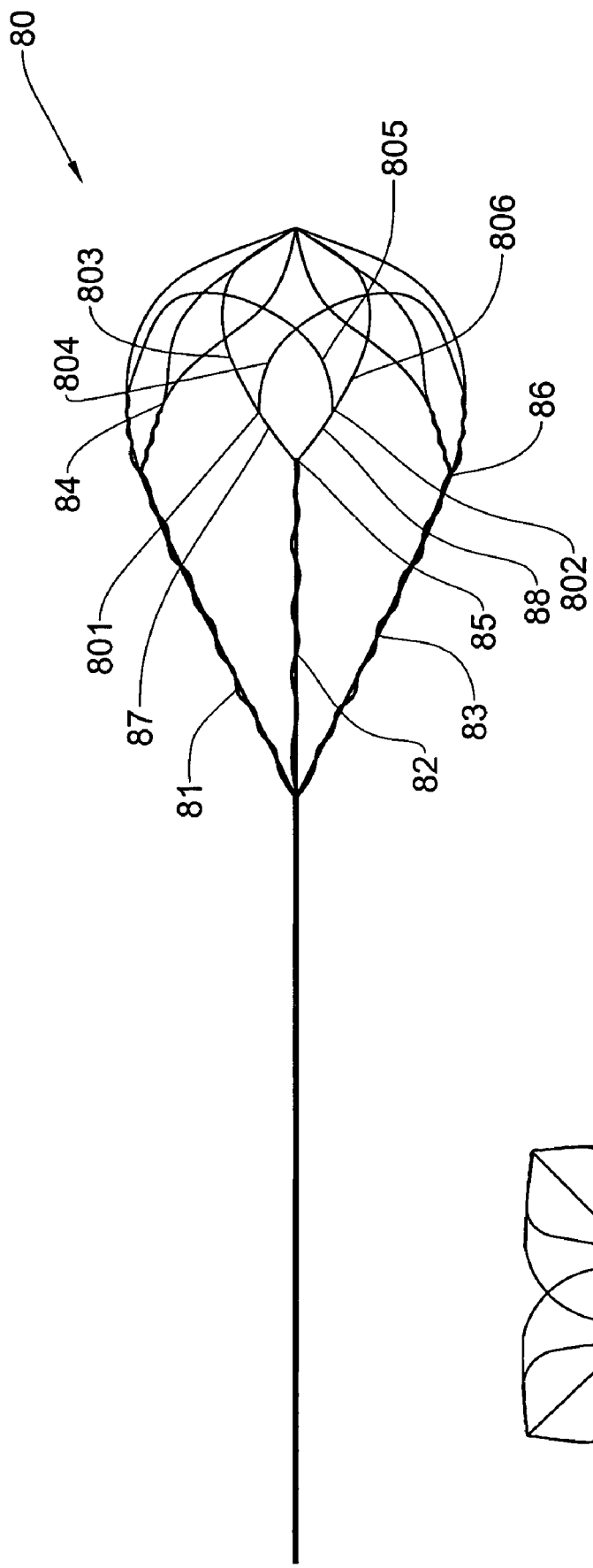
FIGS. 8A and 8B are plan and top schematic views of a longitudinal cross-section, respectively, of a basket according to yet another embodiment of the invention.
Figure 8B:
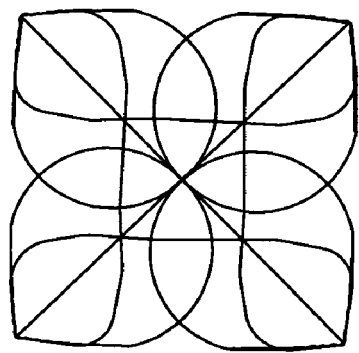

Referring now to FIGS. 8A and 8B, yet another embodiment of the invention is illustrated. According to this embodiment, a retrieval basket 80 includes four strands configured in branches. Only three such strands 81, 82 and 83 can be seen in FIG. 8. Each strand is formed of four entwined wire filaments. The strands 81, 82 and 83 ramify at branching points 84, 85, 86 and result in interlaced loops. For example, the strand 82 ramifies at the branching point 85 into two branches 87 and 88, consisting of two entwined filaments. In turn, the branches 87 and 88 ramify at branching points 801 and 802, and provide loops formed of filaments 803, 804, 805 and 806, respectively. According to this embodiment of the invention, the loops formed thereby are interlaced so as to form a net structure.

Figure 9A:
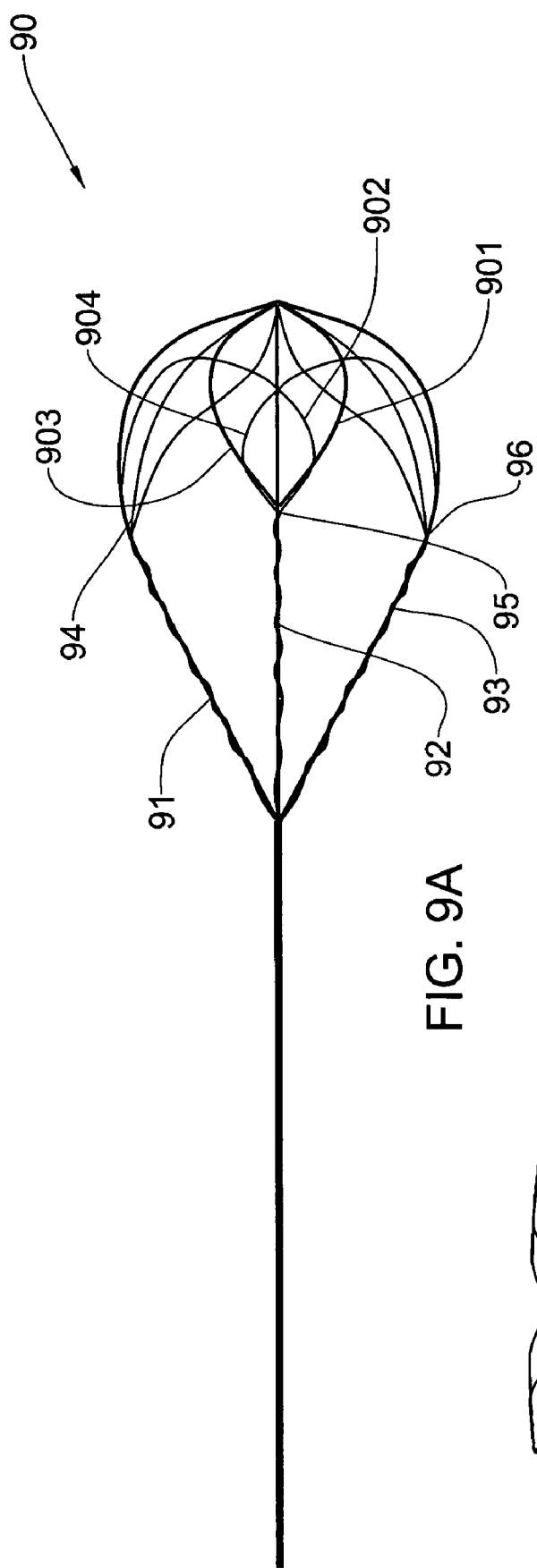
FIGS. 9A and 9B are plan and top schematic views of a longitudinal cross-section, respectively, of a basket according to still further embodiment of the invention.
Figure 9B:
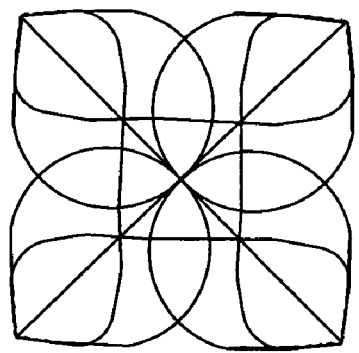

Referring now to FIGS. 9A and 9B, still a further embodiment of the invention is illustrated. According to this embodiment, a retrieval basket 90 includes four strands configured in branches. Only three such strands 91, 92 and 93 can be seen in FIG. 9. Each strand is formed of four entwined wire filaments. These strands ramify at branching points 94, 95, 96 and result in interlaced loops. For example, the strand 92 ramifies at the branching point 95 into the loops formed of filaments 901, 902, 903 and 904. According to this embodiment of the invention, the loops formed thereby are interlaced so as to form a net structure.

Figure 10:
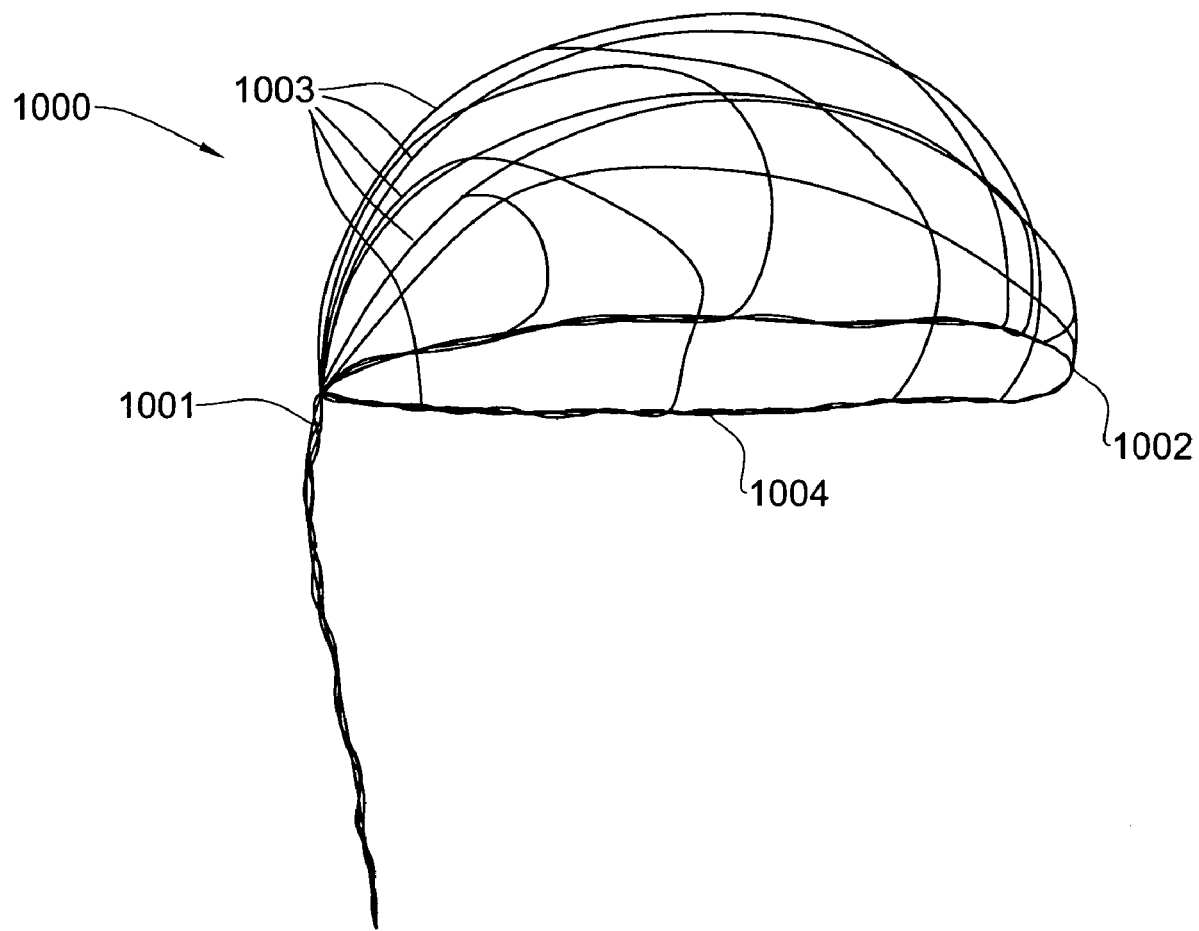
FIG. 10 is a schematic view of a basket according to yet further embodiment of the invention.

Referring now to FIG. 10, still a further embodiment of the invention is illustrated. According to this embodiment, a retrieval basket 1000 comprises a spoon-like structure having a proximal end 1001 and a distal end 1002 and formed of a plurality of wire filaments. In a region of the structure at the proximal end, the filaments are bound and form a plurality of strands 1003. The filaments extend from the proximal end towards the distal end and are configured in the form of interlaced loops so as to form a net structure. The filaments, which originate from the proximal end, arrive at the proximal end after winding. According to this embodiment, one strand (a strand 1004) of the plurality of strands 1003 is common for all the filaments.

Figure 11:
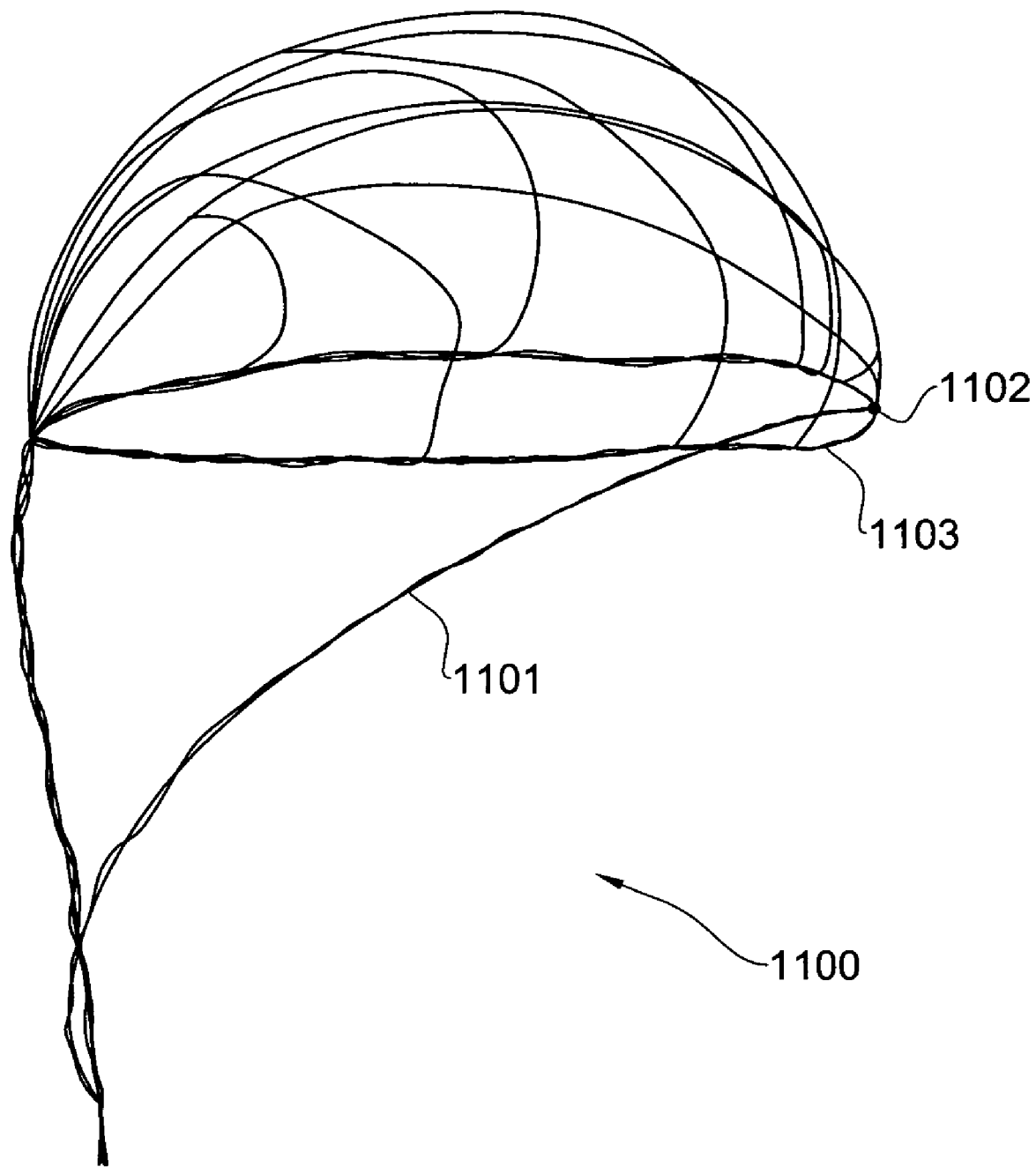
FIG. 11 is a schematic view of a basket according to yet further embodiment of the invention.

Referring now to FIG. 11, still a further embodiment of the invention is illustrated. According to this embodiment, in addition to the structure of the basket 1000 shown in FIG. 10, a structure of a retrieval basket 1100 further includes a supporting cable 1101 connected to a strand 1103 for imparting additional structural rigidity to the basket when it is opened. For example, the supporting cable 1101 can include one ore more filaments and be connected to strand 1103 at a distal end 1102.

Referring now to FIGS. 12A-12F, it will be explained how individual wire filaments, from which the loops are made, could overlap and/or interlace. Note that the term "overlap" herein is assigned to such arrangement of the filaments, in which one element passes through the perpendicularly directed filament, i.e., one of the filaments is always over or under the other filament. The term "interlace" herein is assigned to the situation when at least one filament interweaves with the perpendicularly directed filaments, i.e., one of the filaments passes first above the perpendicularly directed filament and then passes under the next perpendicularly directed filament.

In FIGS. 12A-12F different patterns corresponding to a possible arrangement of individual filaments defining the cells are shown schematically and with exaggeration. For the sake of simplicity, the wire filaments are depicted as vertical and horizontal bands overlapping at a right angle and defining orthogonal pattern, consisting of four vertical and four horizontal bands. However, it should be understood that in reality, thin wire filaments form the cells. The filaments are directed with respect to each other not necessarily at a right angle, and their amount is not limited to a four by four pattern.

FIG. 12A shows a pattern in which all wire filaments interlace one with another, i.e. each horizontal wire filament interlaces with all vertical filaments and vice versa. It is seen, for example, that a vertical filament 710 goes first under a horizontal filament 712, then above a horizontal filament 714, then again under a horizontal filament 716 and finally again above a horizontal filament 718. On the other hand the horizontal filament 712 goes first above the vertical filament 710, then under a vertical filament 720, then again above a vertical filament 722 and then again under a vertical filament 724. The rest of filaments are arranged similarly.

FIG. 12B depicts another situation, in which the filaments both interlace and overlap with intersection. It is seen that a vertical filament 726 interlaces with horizontal filaments 728, 730, 734 and overlaps with the perpendicularly directed filament 732.

In FIG. 12C is shown still a new pattern, consisting of overlapped and interlaced filaments. It is seen for this example that two neighboring vertical filaments 736, 738 go under two neighboring horizontal filaments 740, 742 and then go above two next horizontal filaments 744, 746.

FIGS. 12D-12F show further possible patterns, consisting of overlapped and interlaced filaments. In particular, in the pattern shown in FIG. 12F, each filament overlaps with three perpendicular filaments and interlaces with only one filament.

It can be appreciated that the patterns depicted in FIG. 12A and FIG. 12F represent two extreme situations, corresponding respectively to the pattern in which all filaments are interlaced and to the pattern in which only one filament is interlaced, while the other filaments are overlapped.

Having explained various cells patterns, in which the filaments of the loops might be arranged, still another embodiment of the surgical device of the invention will be disclosed. According to this embodiment, a process of opening the baskets having the topology described above is ensured not by elasticity of the material of the filaments as in the previous embodiments, but by virtue of the thermo-mechanical shape memory characteristic of the material from which the filaments are made. An example of such a material is a super elastic alloy based on Ni and Ti, like Nitinol (e.g., Nitinol SE508 Wire commercially available from Nitinol Devices & Components) or any other suitable commercially available alloy having shape memory ability, i.e. the ability to return to some previously defined shape or size when subjected to the appropriate thermal procedure.

Figure 13:
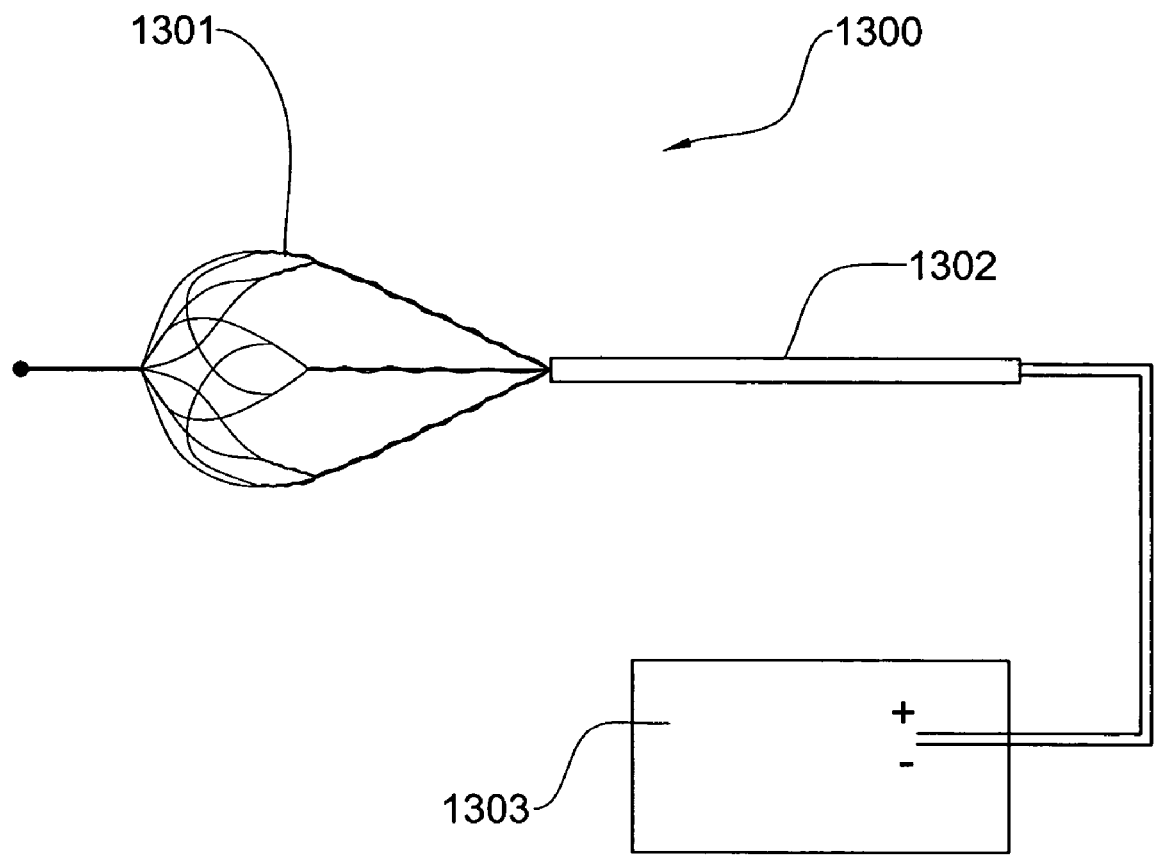
FIG. 13 is a schematic view of a system for control of a surgical device with a basket made of a material with thermomechanical shape memory effect, according to one embodiment of the preset invention.

Referring to FIG. 13, a schematic view of a system for control of a surgical device 1300 with a basket made of a material with thermo-mechanical shape memory effect is shown, according to one embodiment of the preset invention. An example of such a material is Nitinol SM495 Wire commercially available from Nitinol Devices & Components. It should be noted that the blocks in FIG. 13 are intended as functional entities only, such that the functional relationships between the entities are shown, rather than any physical connections and/or physical relationships.

According to this embodiment of the invention, the system includes a retrieval basket 1301 and a basket control means 1302. The basket control means 1302 includes a controllable power supply source 1303 coupled to filaments of the basket 1301 for passing an electric current therethrough that is capable of causing them to change their shape due to heating. The manner of coupling the power supply source 1303 to the filaments and control of the surgical device is known per se (see, for example, WO 92/16153), and therefore will not be expounded hereinbelow.

According to one embodiment of the invention, the filaments of the basket are covered by an insulating layer. The insulating layer can, for example, be made of Teflon. The advantage of Teflon is its thermal resistance and low coefficient of mechanical friction, which leads to an additional reduction of traumatism. Furthermore, manufacturing of the basket filaments from Nitinol renders the whole basket ability to undergo reversible deformation up to 10%, which is close to the dilatation ability of living tissues. It can be readily appreciated that a basket made of Nitinol becomes compatible both biologically and mechanically with the adjacent tissues, since it is more capable of coping the topography of the organ in which the basket resides. By virtue of improved compatibility the basket becomes less traumatic. Still a further advantage of using Nitinol is associated with the "superelastic" properties of this material and the capability of this alloy to improve its "rigidity" when the temperature increases. Introducing of a catheter with deployed therein Nitinol basket into a body organ, having a temperature higher than the ambient temperature increases elasticity of the basket and its dilatation ability, which improves the ability of the basket to reliably entrap and retain the object or calculi to be retrieved. It should be also mentioned, that due to the "superelastic" properties of Nitinol, surgical extractors employing baskets made of this material have a longer service life than extractors with baskets made of stainless steel.

It can be appreciated that by virtue of the above-described construction of the retrieval basket, provided with overlapping loops, the whole surgical apparatus of the present invention becomes very simple, inexpensive, easy and reliable in operation. The surgical tool of the invention is capable of conveniently entrapping and reliably retaining both small and large objects and at the same time, it is less traumatic due to basket's improved structural rigidity and dilatation ability.

As such, those skilled in the art to which the present invention pertains, can appreciate that while the present invention has been described in terms of preferred embodiments, the concept upon which this disclosure is based may readily be utilized as a basis for the designing of other structures and processes for carrying out the several purposes of the present invention.

It should be understood that the device of the present invention is not limited to the urological treatment of a human body. It can be successfully employed for surgical treatments of animals as well. Furthermore, the present invention is not limited strictly to extracting calculi during urological treatment. It is suitable for other surgical treatments, which might require retrieval of foreign objects from the body systems, e.g. from blood vessels etc.

Moreover, the present invention is not limited to medical devices, and the extractor device can be used to extract any type of article from a wide range of inaccessible locations such as inside a pipe or tube (for example, the waste outlet of a domestic sink) or inside a chamber within a large piece of machinery which would be difficult to dismantle.

Also, it is to be understood that the phraseology and terminology employed herein are for the purpose of description and should not be regarded as limiting.

It is important, therefore, that the scope of the invention is not construed as being limited by the illustrative embodiments set forth herein. Other variations are possible within the scope of the present invention as defined in the appended claims and their equivalents.

The invention claimed is:

1. A retrieval basket for entrapping and retaining an object located in a body for its extraction therefrom, the basket comprising a structure having a proximal end and a distal end, said retrieval basket being constituted by a plurality of filaments extending from the proximal end towards the distal end, said filaments are made of a material that imparts structural rigidity and dilatation abilities to the basket when the basket is opened, wherein said filaments are bound together in the vicinity of the proximal end to define a plurality of strands each having a plurality of filaments, said plurality of strands have branching points in which they ramify into loops having various shapes and sizes, at least a part of the loops are interlaced at spaced points so as to define a net at least in the vicinity of, and spaced from, the distal end.

2. The basket of claim 1 wherein the net is formed of cells having a hole size decreasing from the proximal end towards the distal end.

3. The basket of claim 1 wherein the structure is fabricated from a single length of wire.

4. The basket of claim 1 wherein the structure is fabricated from several wires.

5. The basket of claim 1 wherein one of the strands of said plurality of strands is common for all the filaments.

6. The basket of claim 5 wherein said structure has a spoon shape.

7. The basket of claim 1 wherein at least a part of the filaments, which originate from the proximal end, also arrive at the proximal end after winding.

8. The basket of claim 1 wherein said structure has a parachute shape.

9. The basket of claim 1 wherein at least some of the loops are twisted and configured in a figure 8 configuration.

10. The basket of claim 1 wherein said filaments are bound together at said distal end to form a basket tip.

11. The basket of claim 1 wherein said filaments are bound together at said proximal end to form a pushing element.

12. The basket of claim 1 wherein the filaments are made of metallic material.

13. The basket of claim 12 wherein said metallic material has thermo-mechanical shape memory characteristic.

14. The basket of claim 13 wherein said metallic material has superelastic characteristic.

15. The basket of claim 12 wherein said metallic material is selected from NiTi based alloy and stainless steel.

16. The basket of claim 1 wherein the filaments are made of non-metallic material.

17. The basket of claim 16 wherein said non-metallic material is a polyamide resin.

18. The basket of claim 1 wherein the filaments are covered by a coating layer.

19. A surgical device for removing a foreign object from a body, comprising:
the retrieval basket according to claim 1; and
a basket control assembly coupled to the basket at the proximal end, comprising a tubular sheath adapted to penetrate into the body for reaching the object, and a manipulator for manipulating the basket via a pushing element arranged within the sheath for extracting the object from the body, where the assembly is configured for retracting the basket within the sheath and protracting the basket therefrom for opening the basket.

20. The device of claim 19 wherein said pushing element is constituted by said plurality of filaments extending from said proximal end towards the manipulator.

21. The device of claim 19 wherein said manipulation cable is configured as a separate unit selected from a rod, cable and wire.

22. The device of claim 19 wherein the net is formed of cells having a hole size decreasing from the proximal end towards the distal end.

23. The device of claim 19 wherein the structure is fabricated from a single length of wire.

24. The device of claim 19 wherein the structure is fabricated from several wires.

25. The basket of claim 24 wherein said structure has a spoon shape.

26. The device of claim 19 wherein one of the strands of said plurality of strands is common for all the filaments.

27. The device of claim 19 wherein at least a part of the filaments, which originate from the proximal end, also arrive at the proximal end after winding.

28. The device of claim 19 wherein said structure has a parachute shape.

29. The device of claim 19 wherein at least some of the loops are twisted and configured in a figure 8 configuration.

30. The device of claim 19 wherein said filaments are bound together at said distal end to form a basket tip.

31. The device of claim 30 wherein said metallic material has thermo-mechanical shape memory characteristic.

32. The device of claim 30 wherein said metallic material is selected from NiTi based alloy and stainless steel.

33. The device of claim 19 wherein the filaments are made of metallic material.

34. The device of claim 33 further comprising a controllable power supply source coupled to the filaments for passing electric current therethrough.

35. The device of claim 34 wherein said nom-metallic material is a polyamide resin.

36. The device of claim 35 wherein said coating layer is made of polytetrafluoroethylene.

37. The device of claim 19 wherein the filaments are made of non-metallic material.

38. The device of claim 19 wherein the filaments are covered by a coating layer.

* * * * *